United States Patent
Faries, Jr. et al.

(10) Patent No.: US 6,259,067 B1
(45) Date of Patent: Jul. 10, 2001

(54) TEMPERATURE CONTROL SYSTEM AND METHOD FOR HEATING AND MAINTAINING MEDICAL ITEMS AT DESIRED TEMPERATURES

(75) Inventors: Durward I. Faries, Jr., McLean; Bruce R. Heymann, Vienna; Calvin Blankenship, Centreville, all of VA (US)

(73) Assignee: Medical Solutions, Inc., Chantilly, VA (US)

( * ) Notice: Subject to any disclaimer, the term of this patent is extended or adjusted under 35 U.S.C. 154(b) by 0 days.

(21) Appl. No.: 09/419,664

(22) Filed: Oct. 15, 1999

Related U.S. Application Data

(60) Provisional application No. 60/126,651, filed on Mar. 29, 1999, and provisional application No. 60/104,635, filed on Oct. 16, 1998.

(51) Int. Cl.[7] .............................. A61F 7/00; F27D 11/00; F27D 19/00
(52) U.S. Cl. ...................... 219/428; 219/394; 219/399; 604/114
(58) Field of Search ..................................... 219/385, 386, 219/394, 399, 406, 407, 413, 428; 222/146.5; 312/236, 123, 270.2; 604/114, 291; 126/191, 194

(56) References Cited

U.S. PATENT DOCUMENTS

| | | |
|---|---|---|
| 1,659,719 | 2/1928 | Blake . |
| 2,214,215 | 9/1940 | Watermann et al. . |
| 2,576,874 | 11/1951 | Acton . |
| 2,713,112 | 7/1955 | Mills et al. . |
| 2,741,099 | 4/1956 | Beane . |

(List continued on next page.)

OTHER PUBLICATIONS

Cahill, *New Name New Helmsman*, JEMS, Aug. 1996.
CBi Healthcare Systems, Inc., *Controlled Temperature Cabinet System*, JEMS, Mar. 1997.
Koolatron, *P–34 PC–3 Precision Control Thermoelectric Cooler/Warmer*, Jan. 1998.

(List continued on next page.)

*Primary Examiner*—Joseph Pelham

(57) ABSTRACT

A temperature control system includes a cabinet or system housing having a plurality of drawers for containing intravenous solution bags or other medical items. Each drawer is individually controlled, and generally includes a window and a plurality of sub-compartments with each sub-compartment accommodating an intravenous solution bag or other medical item. The drawers are each pivotable relative to the system housing to permit access to the sub-compartments, while the drawer windows enable the intravenous solution bags to be viewed during heating. A heating element is typically disposed beneath each drawer bottom wall to apply heat to walls of corresponding sub-compartments and evenly distribute heat to intravenous solution bags contained within those sub-compartments. Each drawer is associated with a controller that controls the heating element to apply heat to the corresponding drawer sub-compartments in accordance with a comparison between desired and measured temperatures associated with that drawer. Alternatively, the system may include a single common controller to control the heating element of each drawer based on the desired and measured temperatures associated with that drawer. The temperature control system may be mounted on a wall, intravenous (IV) pole, transportable cart or other suitable structure via a support mechanism. In addition, several temperature control systems may be mounted in a stacked or other arrangement on a transportable cart or other structure to provide heating capability for numerous medical items.

36 Claims, 8 Drawing Sheets

U.S. PATENT DOCUMENTS

| | | | |
|---|---|---|---|
| 2,885,526 | * | 5/1959 | Paulding .................... 219/394 |
| 2,994,760 | | 8/1961 | Pecoraro et al. . |
| 3,051,582 | * | 8/1962 | Muckler et al. ............. 219/386 |
| 3,193,339 | * | 7/1965 | Cooper ....................... 312/123 |
| 3,241,603 | | 3/1966 | Nagata . |
| 3,255,812 | | 6/1966 | Bayane et al. . |
| 3,329,202 | | 7/1967 | Birman . |
| 3,353,589 | | 11/1967 | Tope et al. . |
| 3,386,498 | | 6/1968 | Funfstuck . |
| 3,485,245 | | 12/1969 | Lahr et al. . |
| 3,536,132 | | 10/1970 | Pecoraro et al. . |
| 3,590,215 | | 6/1971 | Anderson et al. . |
| 3,612,165 | | 10/1971 | Haynes . |
| 3,713,302 | | 1/1973 | Reviel . |
| 3,777,187 | | 12/1973 | Kohn . |
| 3,826,305 | | 7/1974 | Fishman . |
| 3,858,106 | | 12/1974 | Launius . |
| 3,879,171 | * | 4/1975 | Tulis ........................... 219/521 |
| 4,189,995 | | 2/1980 | Löhr et al. . |
| 4,233,495 | | 11/1980 | Scoville et al. . |
| 4,309,592 | | 1/1982 | Le Boeuf . |
| 4,318,276 | | 3/1982 | Sato et al. . |
| 4,328,676 | | 5/1982 | Reed . |
| 4,364,234 | | 12/1982 | Reed . |
| 4,407,133 | | 10/1983 | Edmonson . |
| 4,419,568 | * | 12/1983 | Overloop ..................... 219/386 |
| 4,455,478 | | 6/1984 | Guibert . |
| 4,464,563 | | 8/1984 | Jewett . |
| 4,495,402 | | 1/1985 | Burdick et al. . |
| 4,523,078 | | 6/1985 | Lehmann . |
| 4,605,840 | | 8/1986 | Koopman . |
| 4,657,004 | | 4/1987 | Coffey . |
| 4,678,460 | | 7/1987 | Rosner . |
| 4,707,587 | | 11/1987 | Greenblatt . |
| 4,726,193 | | 2/1988 | Burke et al. . |
| 4,745,248 | | 5/1988 | Hayes . |
| 4,801,777 | | 1/1989 | Auerbach . |
| 4,823,554 | | 4/1989 | Trachtenberg et al. . |
| 4,874,033 | | 10/1989 | Chatelain et al. . |
| 4,906,816 | | 3/1990 | van Leerdam . |
| 4,910,386 | | 3/1990 | Johnson . |
| 4,935,604 | | 6/1990 | Allen et al. . |
| 4,961,320 | | 10/1990 | Gutmann . |
| 5,061,241 | | 10/1991 | Stephens, Jr. et al. . |
| 5,061,630 | | 10/1991 | Knopf et al. . |
| 5,081,697 | | 1/1992 | Manella . |
| 5,106,373 | | 4/1992 | Augustine et al. . |
| 5,108,372 | | 4/1992 | Swenson . |
| 5,183,994 | | 2/1993 | Bowles, Sr. et al. . |
| 5,195,976 | | 3/1993 | Swenson . |
| 5,217,064 | | 6/1993 | Kellow et al. . |
| 5,243,833 | | 9/1993 | Coelho et al. . |
| 5,263,929 | | 11/1993 | Falcone et al. . |
| 5,276,310 | | 1/1994 | Schmidt et al. . |
| 5,282,264 | | 1/1994 | Reeves et al. . |
| 5,297,234 | | 3/1994 | Harms et al. . |
| 5,315,830 | | 5/1994 | Doke et al. . |
| 5,333,326 | | 8/1994 | Faries, Jr. et al. . |
| 5,345,923 | | 9/1994 | Luebke et al. . |
| 5,364,385 | | 11/1994 | Harms et al. . |
| 5,381,510 | | 1/1995 | Ford et al. . |
| 5,397,875 | | 3/1995 | Bechtold, Jr. . |
| 5,408,576 | | 4/1995 | Bishop . |
| 5,483,799 | | 1/1996 | Dalto . |
| 5,572,873 | | 11/1996 | Lavigne et al. . |
| 5,653,905 | * | 8/1997 | McKinney .................... 219/399 |
| 5,729,653 | | 3/1998 | Magliochetti et al. . |
| 5,910,210 | | 6/1999 | Violi et al. . |
| 5,924,289 | | 7/1999 | Bishop, II . |
| 5,977,520 | * | 11/1999 | Madson, Jr. et al. ......... 219/429 |
| 5,986,239 | * | 11/1999 | Corrigan, III et al. ........ 219/385 |

OTHER PUBLICATIONS

Koolatron, *Canadian company announces the release of a precision control unit*, Aug. 1997.

Anton, *500 miles from nowhere, it'll give you a cold drink or a warm burger...*,Technology Update, 1993.

Koolatron, 1997 U.S. $ Price List, 1997.

Kellow et al, *Drug Adulteration In Prehospital Emergency Medical Services*, Oct. 1994.

CBi Medical, Inc., *IV Fluid Warmer Model 8362*, 1992.

\* cited by examiner

TEMPERATURE CONTROL SYSTEM AND METHOD FOR HEATING AND MAINTAINING MEDICAL ITEMS AT DESIRED TEMPERATURES

CROSS-REFERENCE TO RELATED APPLICATIONS

This application claims priority from U.S. Provisional Patent Application Ser. No. 60/104,635, entitled "Temperature Control System and Method for Heating and Maintaining Medical Items at Desired Temperatures", filed Oct. 16, 1998, and from U.S. Provisional Patent Application Ser. No. 60/126,651, entitled "Temperature Control System and Method for Heating and Maintaining Medical Items at Desired Temperatures in Various Locations", filed Mar. 29, 1999. The disclosures of the above-mentioned provisional applications are incorporated herein by reference in their entireties.

BACKGROUND OF THE INVENTION

1. Technical Field

The present invention pertains to systems for heating medical items. In particular, the present invention pertains to a system for heating and maintaining medical solution containers (e.g., bags or bottles containing saline or intravenous (IV) solutions, antibiotics or other drugs, blood, etc.) or other medical items (e.g., instruments, blankets, etc.) at desired temperatures.

2. Discussion of Related Art

Generally, various items are required to be heated prior to utilization in a medical procedure to prevent thermal shock and injury to a patient. These items typically include intravenous solution, surgical instruments, bottles and blankets. In order to provide the necessary heated items for use in medical procedures, medical personnel may utilize several types of warming systems to heat items toward their operational temperatures. For example, ovens may be disposed within operating rooms to heat items to desired temperatures. Further, U.S. Pat. No. 4,495,402 (Burdick et al) discloses a warmer for heating wet dressings and other articles disposed within a heating and storage compartment. The articles are arranged within the compartment in stacked relation and disposed on a plate that is supplied with thermal energy from a heater. The plate includes a center aperture whereby a first thermal sensor is disposed in the aperture in contact with a bottommost article. Control circuitry is disposed beneath the plate to control the heater to maintain temperature of the bottommost article at a desired level based on the temperatures sensed by the first thermal sensor and a second thermal sensor responsive to heater temperature.

U.S. Pat. No. 5,408,576 (Bishop) discloses an intravenous fluid warmer having a cabinet structure to accommodate a plurality of intravenous fluid bags. A temperature sensor and pad of heating filaments are disposed within the cabinet structure, whereby the temperature sensor enables automatic temperature regulation of the pad of heating filaments to heat the intravenous fluid bags. The heating filaments are covered by a rubber layer to prevent melting of the bags during heating. A temperature indicator disposed on the cabinet structure permits a user to ascertain when a desired temperature is attained, whereby an intravenous fluid bag is removed from the intravenous fluid warmer via an opening defined in a side of the cabinet structure.

The warming systems described above suffer from several disadvantages. In particular, ovens typically do not have a high degree of accuracy or control, thereby enabling use of items having temperatures incompatible with a medical procedure and possibly causing injury to a patient. Further, the Burdick et al and Bishop warmers employ heaters that generally contact a particular portion of an article being heated, thereby heating articles in an uneven manner and enabling formation of hot spots. Moreover, the Burdick et al and Bishop warming systems heat items simultaneously to only a single desired temperature, thereby being incompatible for applications requiring various items to be heated to different temperature ranges.

The present invention overcomes the aforementioned problems and provides several advantages. For example, the present invention evenly distributes heat among intravenous solution bags or other medical items contained within system drawer sub-compartments, thereby avoiding creation of "hot spots" and "cold spots" and ensuring relatively uniform heating of the entire bag with enhanced temperature control. Further, each system drawer includes a window to enable viewing of the intravenous solution bags or other medical items during heating, while the system drawers facilitate easy access to the medical items within the system. In addition, the present invention incurs low operating costs, while providing versatility since the system drawers are each individually controlled to enable the system to heat intravenous solution bags or various other medical items to the same or different desired temperatures.

OBJECTS AND SUMMARY OF THE INVENTION

Accordingly, it is an object of the present invention to simultaneously maintain various items at different desired temperatures for use in medical procedures.

It is another object of the present invention is to simultaneously maintain various items at different desired temperatures for use in medical procedures via a temperature control system including individually controlled drawers, whereby each drawer is maintained at an associated desired temperature.

Yet another object of the present invention is to heat a medical item to a desired temperature by uniformly distributing heat about the medical item, thereby avoiding creation of "hot spots" and "cold spots".

Still another object of the present invention is to uniformly distribute heat about a medical item within a system drawer sub-compartment by conducting heat from a sub-compartment bottom wall along sub-compartment side walls.

A further object of the present invention is to mount a temperature control system on a wall, intravenous (IV) pole, transportable cart or other support structure, via a support mechanism, to enable heating of medical items at various locations.

Yet another object of the present invention is to mount a plurality of temperature control systems in stacked or other relation on a transportable cart or other support structure to enable heating of numerous medical items to desired temperatures at various locations.

The aforesaid objects may be achieved individually and in combination, and it is not intended that the present invention be construed as requiring two or more of the objects to be combined unless expressly required by the claims attached hereto.

According to the present invention, a temperature control system includes a cabinet or system housing having a plurality of drawers for containing intravenous solution bags or other medical items. Each drawer is individually controlled, and generally includes a window and a plurality of sub-compartments with each sub-compartment accommodating an intravenous solution bag or other medical item. The drawers are each pivotable relative to the system housing to permit access to the sub-compartments, while the drawer windows enable the intravenous solution bags to be viewed during heating. A heating element is typically disposed beneath each drawer bottom wall to apply heat to walls of corresponding sub-compartments and evenly distribute heat to intravenous solution bags contained within those sub-compartments. Each drawer is associated with a controller that controls the heating element to apply heat to the corresponding drawer sub-compartments in accordance with a comparison between desired and measured temperatures associated with that drawer. Alternatively, the system may include a single common controller to control the heating element of each drawer based on the desired and measured temperatures associated with that drawer. The temperature control system may be mounted on a wall, intravenous (IV) pole, transportable cart or other suitable structure via a support mechanism. In addition, several temperature control systems may be mounted in a stacked or other arrangement on a transportable cart or other structure to provide heating capability for numerous medical items.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

DETAILED DESCRIPTION OF THE PREFERRED EMBODIMENTS

Figure 1:
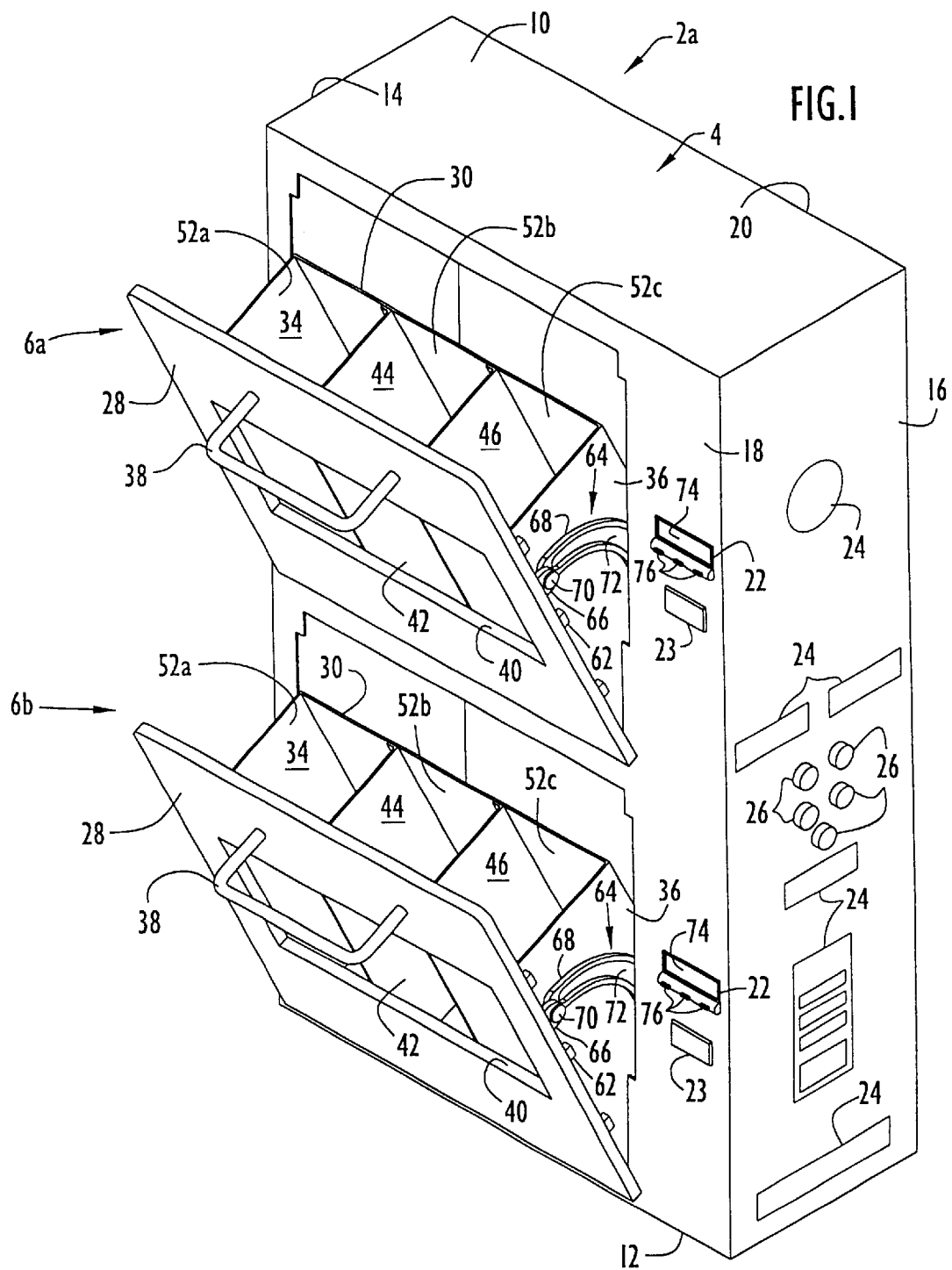
FIG. 1 is a view in perspective of a temperature control system in accordance with the present invention.
Figure 2:
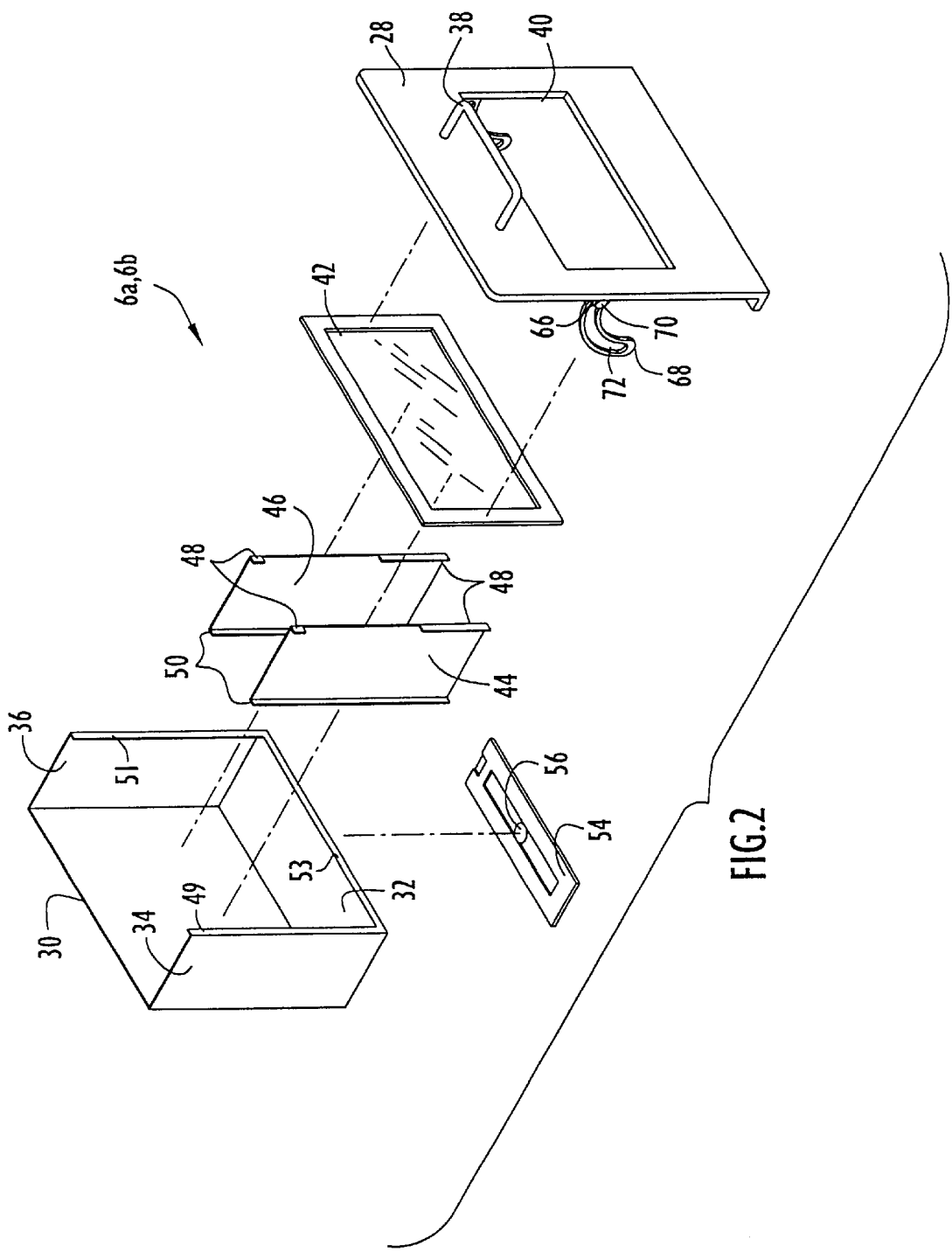
FIG. 2 is an exploded perspective view of a drawer of the system of FIG. 1.

A temperature control system for heating and maintaining medical solution containers (e.g., bags or bottles containing saline or intravenous (IV) solutions, antibiotics or other drugs, blood, etc.) or other medical items (e.g., instruments, blankets, etc.) at desired temperatures is illustrated in FIGS. 1–2. Specifically, temperature control system 2a includes a cabinet or system housing 4 having substantially similar drawers 6a, 6b for enabling placement and removal of medical items, such as intravenous solution bags, within the system and corresponding controllers 22 for individually controlling heating of the drawers to maintain the bags at the same or different desired temperatures. Cabinet 4 is generally in the form of a rectangular box and includes top and bottom walls 10, 12, side walls 14, 16 and front and rear walls 18, 20. The cabinet walls are each substantially rectangular and collectively define a cabinet interior. Further, side wall 16 typically includes a series of labels 24, such as fuse warning labels and labels providing other information, and a plurality of fuse holders 26 for receiving fuses of the system control circuitry described below. The cabinet is typically constructed of electro-galvanized steel (e.g., eighteen gauge) or other suitably sturdy material, and includes, by way of example only, a height of approximately twenty-five inches, a width of approximately fifteen inches and a depth of approximately six inches. However, the cabinet may be of any size or shape. It is to be understood that the terms "top", "bottom", "side", "front", "rear", "horizontal", "vertical", "upper", "lower", "height", "length", "width", "depth", "forward" and the like are used herein merely to describe points of reference and do not limit the present invention to any specific orientation or configuration.

Drawers 6a, 6b are generally disposed in vertical alignment in front wall 18 toward side wall 14, while controllers 22 are each disposed in front wall 18 adjacent a corresponding drawer 6a, 6b and power switch 23 toward side wall 16. Each controller 22 enables entry of a desired or set point temperature associated with a corresponding drawer and controls heating of intravenous solution bags residing within the corresponding drawer based on the associated desired temperature as described below. Each power switch 23 is generally disposed below a corresponding controller 22 and enables power to that controller for heating intravenous solution bags disposed within the corresponding drawer. By way of example only, cabinet 4 includes two each of drawers, associated power switches, controllers and accompanying control circuitry, however, any quantity (e.g., at least one) of drawers, power switches, controllers and control circuitry may be utilized, while the cabinet components may be arranged in any fashion.

Drawers 6a, 6b each include a front wall or door 28, a rear wall 30, a bottom wall 32 and side walls 34, 36. The drawer walls are each substantially rectangular and collectively define a compartment or drawer interior having an open top portion for enabling placement and removal of intravenous solution bags within the drawers. By way of example only, the drawer rear, bottom and side walls define a drawer including a height of approximately eight and one-half inches, a width of approximately ten inches and a depth of approximately three and one-half inches. However, the drawers may be of any size or shape, and the system may include any combination of drawers of different or substantially similar types.

Door 28 includes a handle 38 typically disposed toward the door upper portion, whereby the handle may be implemented by any conventional or other type of handle. Alternatively, the handle may be disposed on the door at any suitable location. Door 28 generally enables a corresponding drawer to pivot into and out of the cabinet as described below, and is typically constructed of electro-galvanized steel (e.g., sixteen gauge) or other suitably sturdy material. The door further includes a substantially rectangular opening 40 covered by a substantially transparent material 42, such as glass or plexiglass, to serve as a window to enable viewing of the intravenous solution bags and maintain heat within the cabinet. By way of example only, door 28 includes a height of approximately eleven and one-half inches, and a width of approximately fourteen and one-half inches, however, the door, opening and transparent material may be of any size or shape.

Divider walls 44, 46 are disposed within each drawer interior to partition that interior into sub-compartments or bins 52a, 52b, 52c. In particular, divider walls 44, 46 extend from rear wall 30 substantially in parallel to, and include dimensions substantially the same as, side walls 34, 36. The front and rear edges of dividers 44, 46 are bent at an angle of approximately ninety degrees relative to the respective divider wall body portions, and extend transversely toward side wall 34 to form ledges 48, 50, respectively. Similarly, the front edges of side walls 34, 36 are bent at an angle of approximately ninety degrees relative to the respective side wall body portions, and extend transversely toward each other to form ledges 49, 51, respectively. Further, the front edge of bottom wall 32 is bent at an angle of approximately ninety degrees relative to the bottom wall body portion, and extends upward toward a drawer upper potion to form ledge 53. Ledges 50 enable the divider walls to interface rear wall 30, while ledges 48 include a recess or gap to permit the divider walls to engage and secure transparent material 42 within opening 40 of door 28. Moreover, ledges 48, 49, 51 and 53 enable the door to interface the drawer side, bottom and divider walls. Each drawer sub-compartment is typically configured to accommodate a single intravenous solution bag, and is defined by the drawer rear, bottom, side and divider walls. Specifically, sub-compartment 52a is defined between side wall 34 and divider wall 44, sub-compartment 52b is defined between divider walls 44, 46 and sub-compartment 52c is defined between divider wall 46 and side wall 36. The drawer side, rear, bottom and divider walls are typically constructed of copper or other suitable heat conducting material to conduct and evenly distribute heat to the intravenous solution bags disposed within the drawer as described below.

A heating element or pad 54 is typically disposed on the underside of each drawer bottom wall 32, whereby the heat applied by the heating pad is conducted by the drawer bottom, side, rear and divider walls to provide an even heat distribution to the intravenous solution bags residing in the sub-compartments of that drawer. In other words, each individual drawer sub-compartment includes bottom, side and rear walls that conduct and directly transmit heat from the heating pad to the intravenous solution bag contained in that sub-compartment, thereby preventing other intravenous solution bags residing in the cabinet from being affected by the applied heat. The application of heat from the sub-compartment walls provides a relatively uniform heat distribution and prevents the occurrence of certain intravenous solution bags (e.g., bags disposed near the heat source) attaining higher temperatures than the remaining bags (e.g., bags disposed at other locations within the cabinet) as is typically present in common single heat source systems. Alternatively, the heating pad may be disposed on the side or rear walls of each drawer.

The heating pad is preferably configured to cover only a portion of a drawer bottom wall, but may include any type of configuration (e.g., strips, bars, segments, include various openings, etc.). A temperature sensor 56 is typically disposed on the underside of each drawer bottom wall 32 generally within the confines of the corresponding heating pad (e.g., the portion of the heating pad not covering the drawer bottom wall). The temperature sensor is preferably implemented by a conventional RTD temperature sensor and measures the temperature of the bottom wall of the corresponding drawer. However, the temperature sensor may be implemented by any conventional or other type of temperature sensor, and may be disposed at any suitable location on or within a drawer. The temperature measurement of sensor 56 is provided to the controller associated with the drawer for control of the corresponding heating pad as described below.

Figure 3:
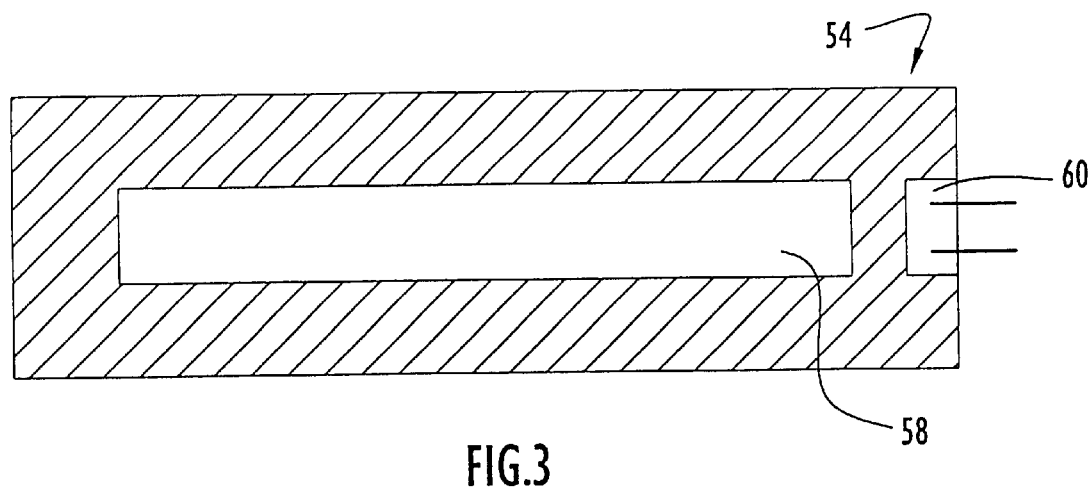
FIG. 3 is a view in elevation of an exemplary heating element of the system of FIG. 1.

An exemplary heating pad of the type employed by the temperature control system is illustrated in FIG. 3. Specifically, heating pad 54 is substantially rectangular and includes a substantially rectangular opening 58. By way of example only, heating pad 54 includes a width or shorter dimension of approximately three inches and length or longer dimension of approximately ten inches, while opening 58 includes a width of approximately one inch and a length of approximately eight inches. A connector 60 is disposed along a heating pad shorter dimension edge to facilitate connections for the heating pad. The heating pad is preferably implemented by a conventional etched foil silicon rubber heater (e.g., 44 watts, 120 VAC) having an extra layer of silicon rubber on the adhesive side. The heating pad further includes a pressure sensitive adhesive for attachment to a drawer bottom wall. Temperature sensor 56 is typically disposed within opening 58 (FIG. 2) to measure the temperature of a corresponding drawer bottom wall as described above. The heating pad may be of any quantity (e.g., at least one), shape, or size, and may include any configuration that covers the entirety or a portion of a corresponding drawer bottom wall. In addition, the heating element or pad may be implemented by any conventional or other type of heater or heating element (e.g., heating coils) to heat the drawers.

Referring back to FIGS. 1–2, side walls 34, 36 of drawers 6a, 6b interface respective doors 28 via posts 62 to secure the drawers to the doors. Each door 28 further includes a pivoting mechanism having a pivot hinge 63 (FIG. 8) and a locking hinge 64 to enable a corresponding drawer to angle forward and pivot outward from the cabinet interior into an open position. In particular, locking hinge 64 includes a receptacle 66 disposed on a corresponding door 28, a curved track or slide 68 and a pin or bolt disposed within the cabinet interior (not shown). Receptacle 66 is disposed toward an intermediate portion of the corresponding door and extends from that door interior surface toward the cabinet interior. The receptacle includes an opening through which a pin or bolt 70 is inserted to connect a proximal end of slide 68 to the corresponding door.

Curved slide 68 typically extends from receptacle 66 of the corresponding door into the cabinet interior and curves toward cabinet bottom wall 12. The slide includes an opening 72 extending along the slide from the receptacle into the cabinet interior, whereby an associated cabinet interior bolt is disposed within and through the opening to enable the corresponding drawer to pivot out of and into the cabinet interior to open and closed positions, respectively. The distal end of the slide, in combination with the associated cabinet interior bolt, serves as a stop to limit pivoting or the forward angle of the corresponding drawer. Locking hinge 64 may be disposed adjacent either side wall 34, 36 of the corresponding drawer, or a door may include dual pivoting mechanisms, whereby a mechanism is disposed adjacent each corresponding drawer side wall. An operator typically grasps handle 38 of a corresponding door and applies force to draw that handle forward, thereby forcing slide 68 of that door forward, while the associated cabinet interior bolt traverses corresponding slide opening 72. When sufficient force is applied to the handle, the distal end of the corresponding slide opening is caused to engage the associated cabinet interior bolt to prevent further pivoting of a corresponding drawer. Conversely, force may be applied to the handle to facilitate pivoting of the corresponding drawer toward the cabinet to a closed position, whereby the corresponding slide is forced into the cabinet interior, while the associated cabinet interior bolt traverses corresponding slide opening 72.

Controllers 22 each typically include a display 74 (e.g., LED or LCD) and a plurality of input devices or buttons 76 for enabling entry of a desired or set point temperature for a corresponding drawer. Input devices 76 are manipulated to enable entry of the desired temperature, while each display 74 may alternatively indicate the actual temperature measured by a corresponding temperature sensor 56 (FIG. 2) or the desired or set point temperature entered by the operator. Display 74 typically displays the measured temperature, and may be directed, via the input devices, to display the set point temperature.

The controllers each essentially implement a feedback control loop to control heating of the corresponding drawers. Specifically, each controller 22 receives a temperature signal from a corresponding temperature sensor 56 indicating the temperature of the corresponding drawer bottom wall. In response to the measured temperature of a corresponding drawer bottom wall being equal to or exceeding the desired temperature associated with that drawer, the corresponding controller disables power to the associated heating element via a solid state relay described below. Conversely, when the measured temperature of the corresponding drawer bottom wall is below the desired temperature associated with that drawer, the corresponding controller enables power to the associated heating element via the solid state relay. Each controller is preferably implemented by a Eurotherm Controls Model 2132 Controller that is generally preprogrammed with a PID (Proportional-Integral-Derivative) control algorithm to control the corresponding heating element based on the measured temperature of the corresponding drawer. However, the controllers may be implemented by any conventional or other processor or circuitry utilizing any control algorithm to control the heating elements.

Figure 4:
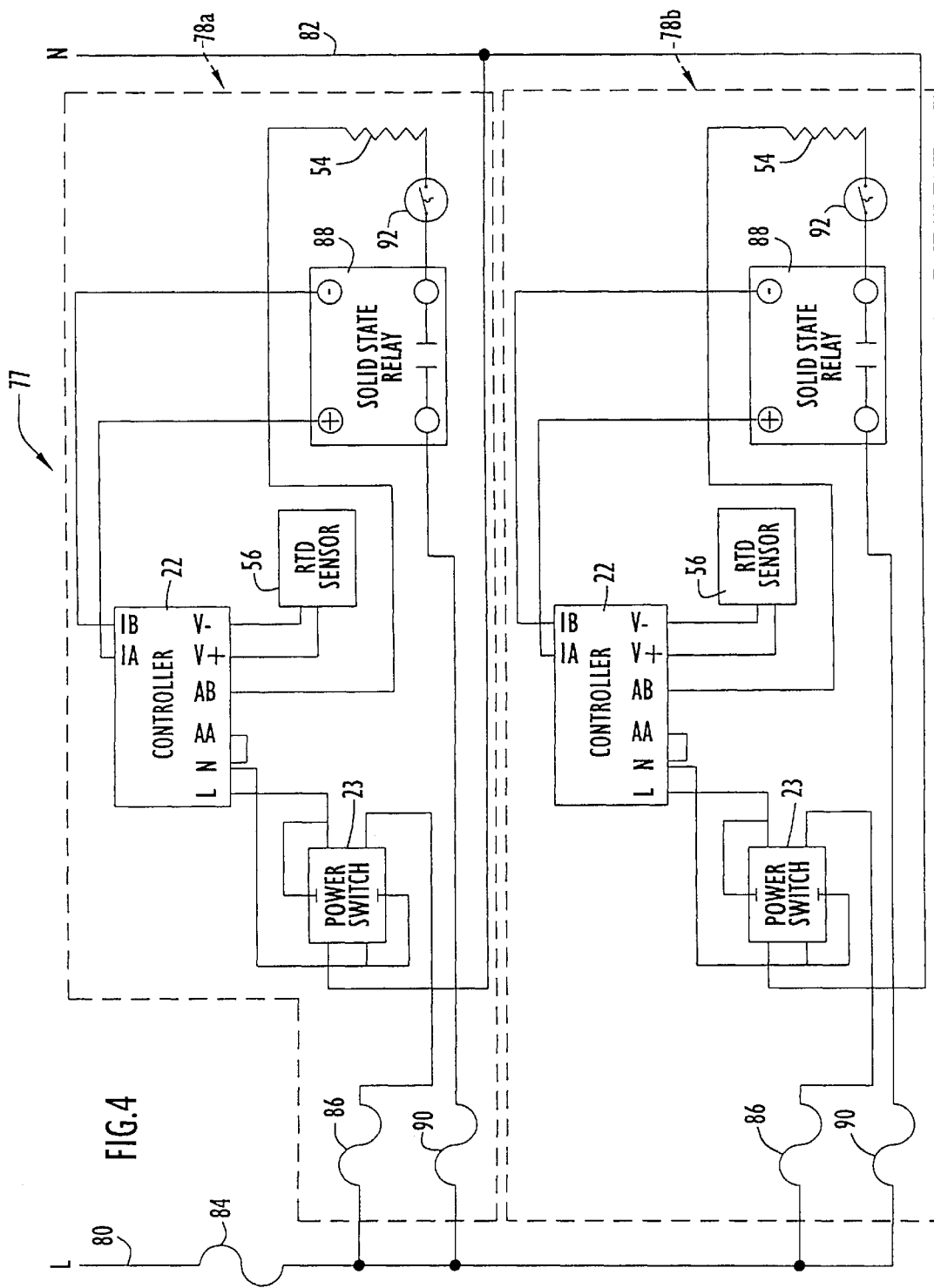
FIG. 4 is an electrical schematic diagram of an exemplary control circuit of the system of FIG. 1.

An exemplary control circuit of the temperature control system is illustrated in FIG. 4. Specifically, system control circuit 77 includes control circuits 78a, 78b to control heating of corresponding drawers 6a, 6b, respectively. The control circuits are disposed between power conductors 80, 82 to enable power to the circuits. Conductor 80 typically supplies a positive potential, while conductor 82 provides a negative or reference potential. A fuse 84, preferably a conventional three Amp fuse, is connected in series with conductor 80 and the control circuits to prevent surges from damaging the circuitry. Control circuit 78a includes conventional power switch 23, controller 22, temperature sensor 56, a conventional solid state relay 88, a conventional temperature cut out switch 92, heating element or pad 54 and conventional fuses 86, 90. In particular, power switch 23 is connected to conductor 80, while fuse 86, typically a two Amp fuse, is connected between the power switch and conductor 80 to prevent damage to the power switch. The power switch is further connected to conductor 82 and controller 22 to enable power to the controller.

Controller 22 receives power from power switch 23 and is further connected to temperature sensor 56, solid state relay 88 and heating pad 54. The temperature sensor measures a corresponding drawer bottom wall temperature and transmits a signal to controller 22 indicating that temperature. The controller controls solid state relay 88 to enable or disable power to heating pad 54 based on the measured temperature as described above. The solid state relay is connected to conductor 80 and heating pad 54, while fuse 90, typically a 0.5 Amp fuse, is connected between the relay and conductor 80 to prevent damage to the relay. Moreover, temperature cut-out switch 92 is connected between the relay and heating pad to disable the heating pad in response to detecting a heating pad temperature in excess of a predetermined threshold. Control circuit 78a may be implemented by any conventional circuitry components performing the above-described functions. Control circuit 78b is connected in parallel with and is substantially similar to control circuit 78a described above to control heating of drawer 6b.

Operation of the temperature control system is described with reference to FIGS. 1–4. Initially, an operator selects intravenous solution bags (e.g., containing intravenous solution) or other medical items for heating within the cabinet and determines appropriate temperatures for the items. The operator subsequently selects a drawer 6a, 6b and enables a corresponding power switch 23, whereby the operator grasps and applies force to handle 38 of the selected drawer to pivot that drawer outward from the cabinet interior to an open position. Intravenous solution bags are disposed within any quantity (e.g., at least one) or combination of corresponding drawer sub-compartments 52a, 52b, 52c such that any one sub-compartment contains a single intravenous solution bag. The selected drawer is subsequently pivoted into the cabinet interior to a closed position. The desired temperature is entered into corresponding controller 22 via input devices or buttons 76. The controller receives signals from corresponding temperature sensor 56 (FIG. 2) and determines appropriate controls for solid state relay 88 (FIG. 4) to enable or disable power to associated heating pad 54 as described above. The heating pad applies heat to the corresponding drawer bottom wall, whereby the drawer rear, side and divider walls conduct heat from the bottom wall to evenly distribute heat to the intravenous solution bags residing within the corresponding drawer sub-compartments as described above.

Controller 22 displays on display 74 the corresponding drawer bottom wall temperature measured by temperature sensor 56, and may be directed to alternatively display the desired temperature based on manipulation of input devices 76. Further, the intravenous solution bags may be viewed through transparent material 42 during heating. When the intravenous solution bags have attained the desired temperature, the selected drawer is pivoted to an open position as described above, whereby the heated bags are removed from sub-compartments of the selected drawer for use, while that drawer is subsequently returned to a closed position. Further, additional intravenous solution bags may replace the removed heated bags within those sub-compartments for heating by the system. It is to be understood that either or both of the drawers may be used and independently controlled in substantially the same manner described above to maintain items at the same or different desired temperatures. Further, any quantity of intravenous solution bags or items may be disposed within the sub-compartments and drawers for heating by the cabinet.

Figure 5:
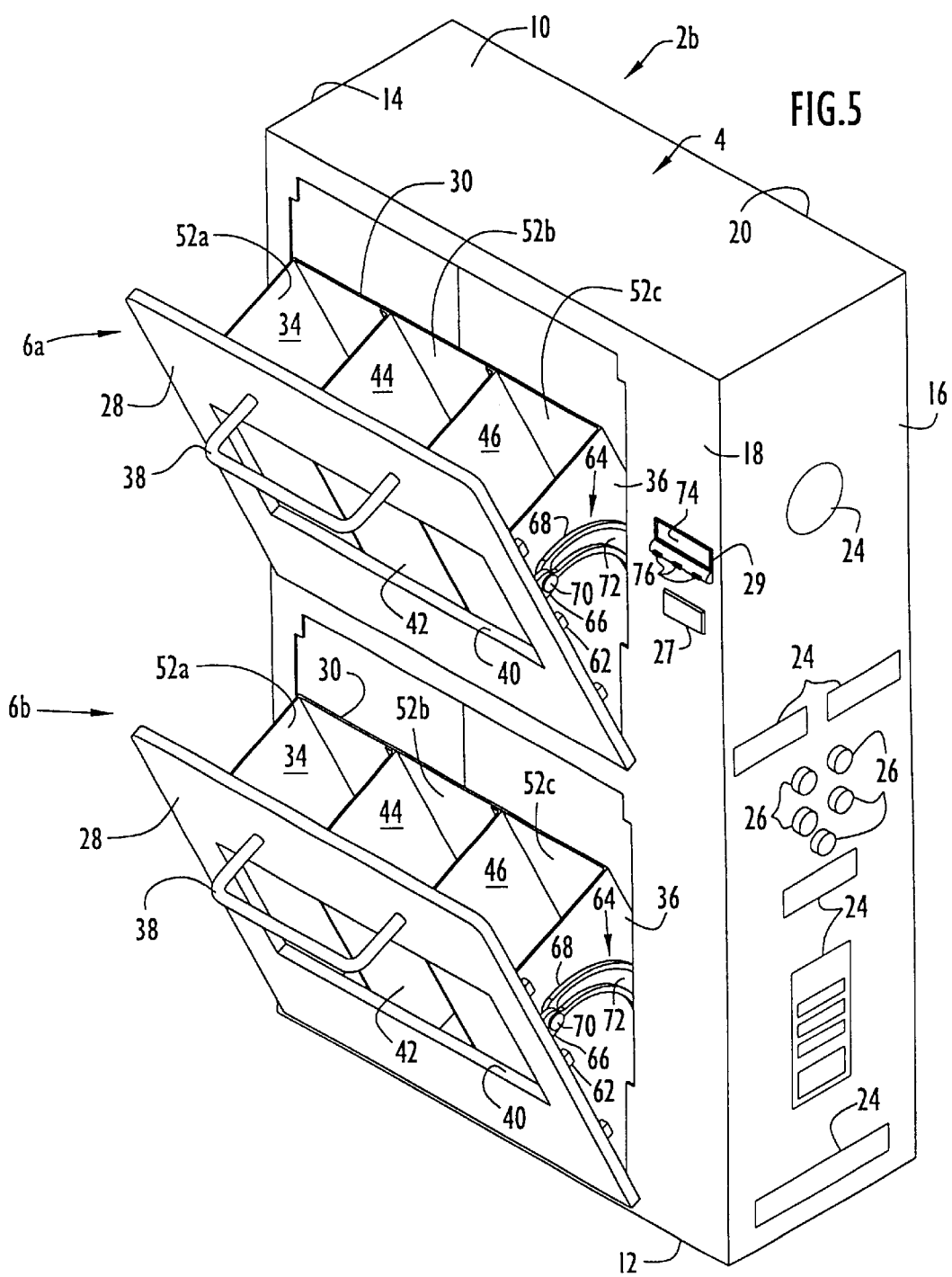
FIG. 5 is a view in perspective of an alternative embodiment of the temperature control system of FIG. 1 having a single controller.

Alternatively, the system may include a single common controller to provide independent control of each drawer as illustrated in FIG. 5. System 2b is substantially similar to system 2a described above except that system 2b includes a single controller 29 for controlling each drawer and a common power switch 27 to enable power to the system. Controller 29 and power switch 27 are typically disposed on front wall 18 adjacent drawer 6a, but may be disposed at any suitable locations on the cabinet. The common power switch is substantially similar to power switches 23 described above, while controller 29 typically includes a display 74 (e.g., LED or LCD) and a plurality of input devices or buttons 76 for enabling entry of desired or set point temperatures for the corresponding drawers. The input devices are manipulated to enable entry of the desired temperatures, while display 74 may indicate the actual temperature of each drawer bottom wall measured by a corresponding temperature sensor 56 (FIG. 2) or the desired or set point temperatures entered by the operator. Display 74 typically displays the measured temperature of each drawer, and may be directed, via the input devices, to display the set point temperatures.

Controller 29 provides independent control for each drawer and essentially implements a feedback control loop to control heating of those drawers. Specifically, controller 29 includes inputs for receiving temperature signals from temperature sensor 56 of each drawer indicating the temperature of a corresponding drawer bottom wall. In response to the measured temperature of a drawer bottom wall being equal to or exceeding the desired temperature entered for a corresponding drawer, the controller disables power to the heating element associated with that drawer via a solid state relay as described below. Conversely, when the measured temperature of the drawer bottom wall is below the desired temperature entered for the corresponding drawer, the controller enables power to the heating element associated with that drawer via the solid state relay. The controller is generally pre-programmed with a fuzzy logic or other type of control algorithm to control each drawer based on the measured temperature of the corresponding drawer bottom wall.

Controller 29 is preferably implemented by a 32A Series Temperature/Process Controller manufactured by Love Controls, a Division of Dwyer Instruments, Inc. Generally, this type of controller provides single set point capability for a process, or dual set point capability (e.g., dependent high and low set points) for the same process, and displays the set point and actual or process temperatures. However, in order to employ this type of controller within the present invention, the 32A Series Controller has been slightly modified. In particular, the alarm relay and associated circuits of the 32A Series Controller have been removed to permit insertion of loop circuitry, thereby enabling independent operation of plural set points. Further, the 32A Series Controller has been modified to display the actual temperature of each drawer bottom wall, while the set point temperatures entered for the drawers may be displayed by manipulating input devices 76. In addition, the options typically available for the 32A Series Controller have not been enabled. It is to be understood that the controllers of the present invention may each be implemented by any quantity of conventional or other processors or circuitry utilizing any control algorithm to control the drawers, whereby the processors or circuitry may accommodate any quantity of heaters, drawers or set points.

An exemplary control circuit for system 2b is substantially similar to the circuit described above for FIG. 4 except that power switches 23 and associated fuses 86 are replaced by a single common power switch 27 (FIG. 5) and an associated fuse, and controllers 22 are replaced by a single controller 29. Specifically, power switch enables power to each drawer and the controller from power conductors 80, 82 (FIG. 4) in substantially the same manner described above for power switches 23. A fuse, similar to fuse 86 described above, is connected between the positive potential power conductor and power switch 27 to prevent damage to the power switch. Controller 29 is connected to power switch 27 and the temperature sensor, heater, and solid state relay associated with each drawer. The controller receives temperature signals from the temperature sensor of each drawer and controls the heating element associated with that drawer, via a corresponding solid state relay, in substantially the same manner described above based on the measured temperature of the corresponding drawer.

Figure 6:
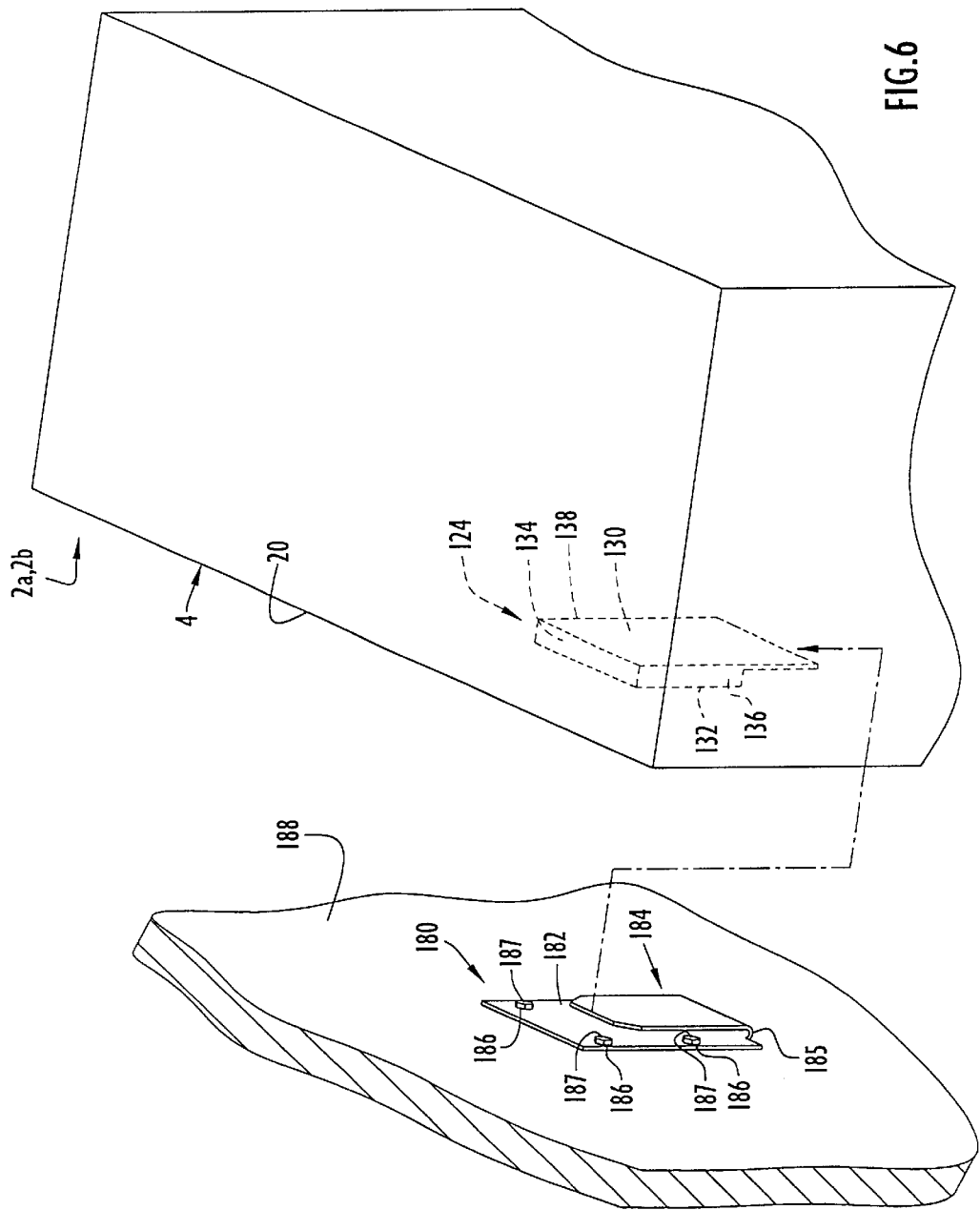
FIG. 6 is an exploded view in perspective of a support mechanism for mounting a temperature control system on a wall or other suitable structure according to the present invention.
Figure 7:
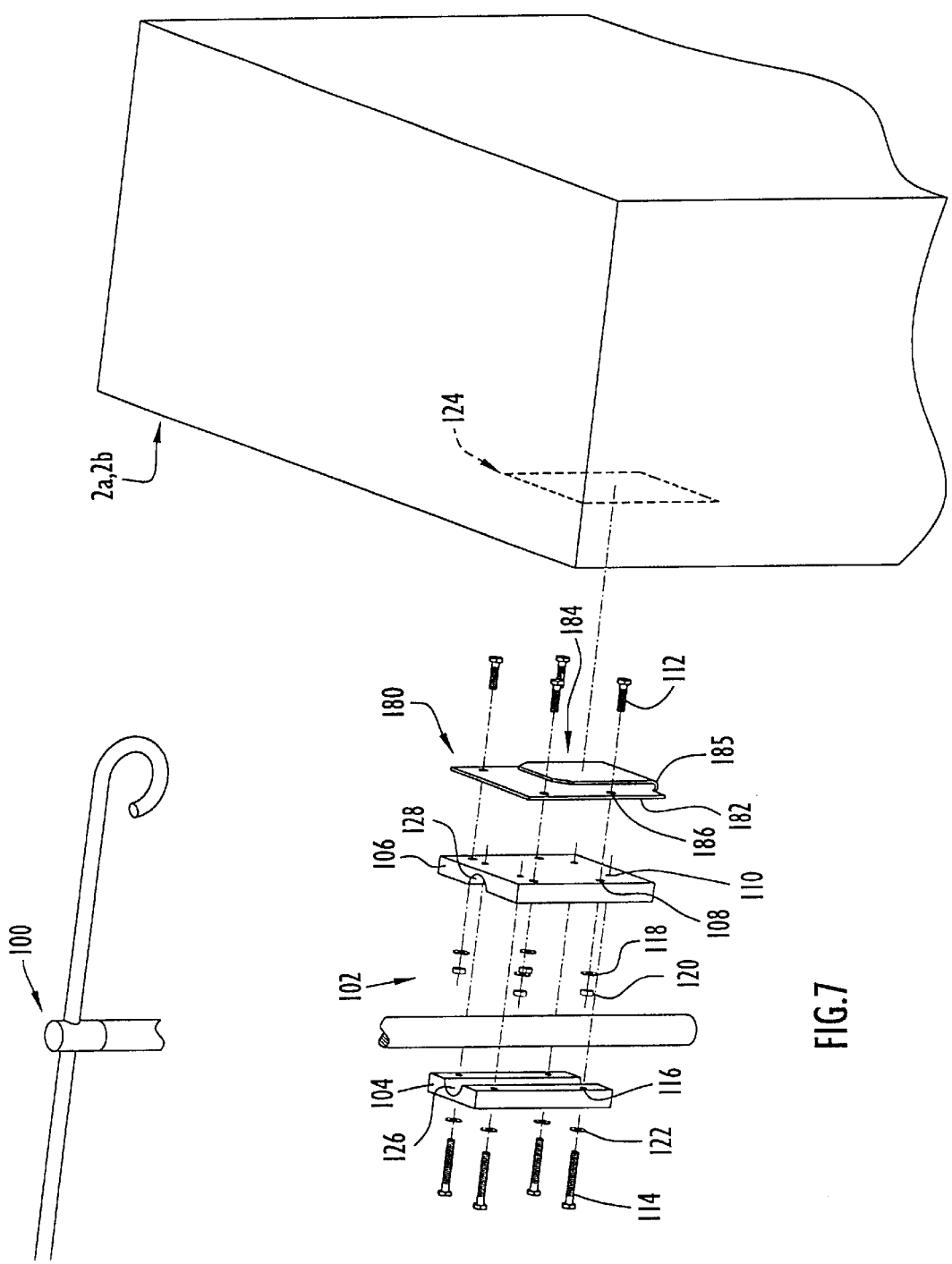
FIG. 7 is an exploded view in perspective of a temperature control system mounted on an intravenous (IV) pole according to the present invention.

The temperature control systems described above may be mounted on a wall or various other structures via a support mechanism as illustrated in FIG. 6. Specifically, a support mechanism 180 includes a base 182 and an engagement member 184. Base 182 is substantially rectangular and includes a series of holes 186 (e.g., preferably four) arranged in a box-like configuration, whereby a hole 186 is defined in the base toward the upper and lower portions of each base side edge. The holes receive bolts or screws 187 to mount the support mechanism on a wall 188 or other structure. Engagement member 184 is typically formed integral with and extends forwardly from the base. In the preferred embodiment, engagement member 184 has a generally rectangular configuration with truncated upper corners and an arcuate lower portion 185 by which member 184 is joined to the base. In particular, the arcuate lower portion extends slightly downward from the base bottom edge and subsequently curves to an upward direction to enable the engagement member upper portion to be spaced from the base by a slight distance and to extend from the curved lower portion substantially parallel to the base. The engagement member dimensions are preferably less than the base dimensions such that the 719 engagement member partially overlies the base central portion residing between holes 186 defined toward the base side edges. The engagement member, in combination with the base, essentially forms a hook-type device for engaging a temperature control system.

A bracket 124 is disposed on a temperature control system 2a, 2b to interface support mechanism 180. In particular, bracket 124 includes a base 130, exposed wall 132, top wall 134 and side walls 136, 138. Base 130 is preferably welded or otherwise secured to a temperature control system 2a, 2b toward the intermediate portion of cabinet rear wall 20, while exposed wall 132 projects substantially parallel to and is separated by a slight distance from the bracket base. The bracket base dimensions are preferably greater than the dimensions of the exposed wall such that the exposed wall generally covers the bracket base upper portion. The bracket top and side walls interconnect the bracket base and exposed wall, thereby forming a bracket compartment having an open bottom portion. The bracket compartment dimensions are slightly greater than the dimensions of engagement member 184 such that the engagement member upper portion is received within the bracket compartment. Temperature control system 2a, 2b may be placed on wall 188, whereby engagement member 184 is inserted into the bracket compartment to suspend that temperature control system from the wall. Medical items, such as intravenous solution bags, may subsequently be heated within temperature control system 2a, 2b as described above.

Temperature control systems 2a, 2b may be further mounted on an intravenous (IV) pole as illustrated in FIG.

7. Specifically, support mechanism 180 may be attached to an intravenous (IV) pole 100 via a support frame 102 to enable temperature control system 2a, 2b to be suspended from that pole. The support frame includes a base plate 104 and a mounting plate 106. The base and mounting plates are each substantially rectangular and include respective arcuate channels 126, 128 defined in the respective interior plate surfaces for interfacing pole 100. Mounting plate 106 includes a series of holes 108 (e.g., preferably four) arranged in a box-like configuration, whereby a hole 108 is defined in the mounting plate toward the upper and lower portions of each mounting plate side edge. Support mechanism 180 is positioned adjacent mounting plate 106 with support mechanism holes 186 disposed coincident mounting plate holes 108. Threaded bolts 112 (e.g., preferably four) are inserted through corresponding mounting plate and support mechanism holes 108, 186 while a plurality of washers 118 (e.g., preferably four) are disposed on a corresponding bolt 112 proximate the mounting plate interior surface. A series of substantially annular nuts 120 (e.g., preferably four) are internally threaded to engage the threads of respective bolts 112. Nuts 120 each engage a corresponding bolt 112 to secure the support mechanism to mounting plate 106.

Base plate 104 has a height similar to, and a width less than the corresponding dimensions of mounting plate 106, and has a series of holes 116 (e.g., preferably four) arranged in a box-like configuration, whereby a hole 116 is defined in the base plate toward the upper and lower portions of each base plate side edge. Holes 116 enable base plate 104 to be secured to mounting plate 106, whereby the mounting plate further includes a set of corresponding holes 110 (e.g., preferably four). Holes 110 are similarly arranged in a box-like configuration, whereby a hole 110 is defined in the mounting plate toward the portions residing between each hole 108 and channel 128. Holes 110 are each internally threaded for engaging fastening devices, such as screws or bolts. Base and mounting plates 104, 106 are placed about pole 100 such that the pole is positioned between the plates and within plate channels 126, 128, while holes 116 of base plate 104 are disposed coincident holes 110 of mounting plate 106. Threaded bolts 114 (e.g., preferably four) are inserted through corresponding washers 122 (e.g., preferably four) and associated base and mounting plate holes 116, 110. Bolts 114 each are threaded to engage the threads of holes 110, whereby the bolts secure base plate 104 to mounting plate 106. The interconnected base and mounting plates engage pole 100, thereby securing support mechanism 180 to the pole and enabling the support mechanism to suspend temperature control system 2a, 2b via bracket 124 as described above.

Figure 8:
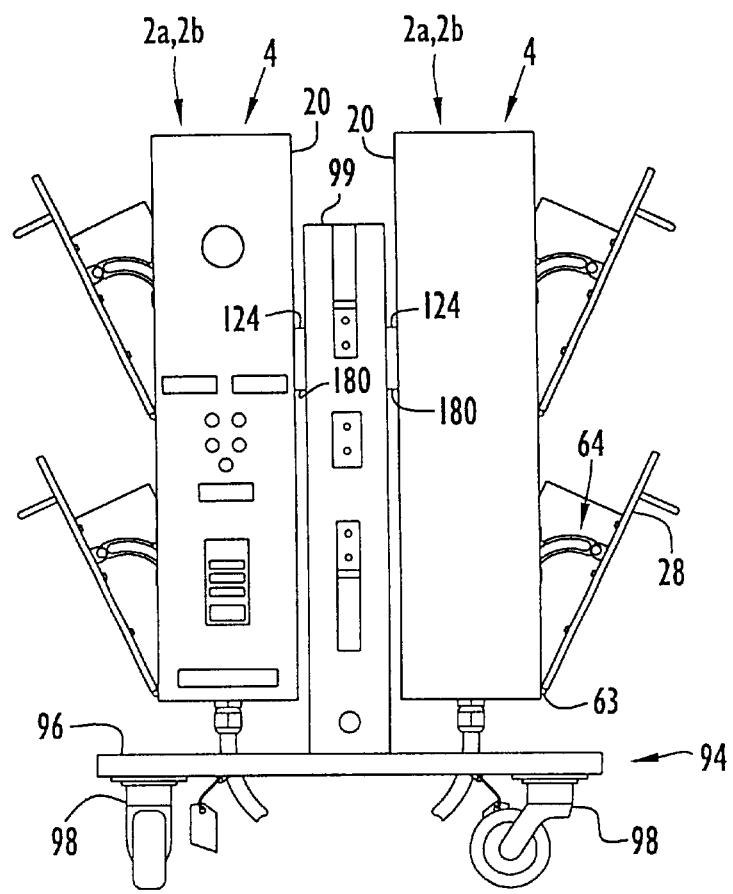
FIG. 8 is a side perspective view of plural temperature control systems mounted on a transportable cart in accordance with the present invention.
Figure 9:
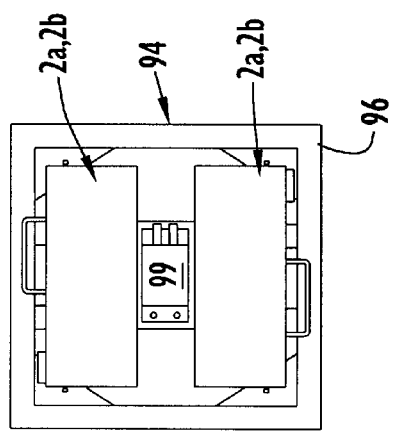
FIG. 9 is a top view of the temperature control systems of FIG. 8 mounted on the transportable cart.

The temperature control systems described above may be further configured to be transportable as illustrated, by way of example only, in FIGS. 8–9. Specifically, a pair of temperature control systems may be disposed on a cart 94 or other transportable device to enable the systems to be transportable. Each member of the system pair may be implemented by any of the temperature control systems 2a, 2b described above. Cart 94 typically includes a substantially rectangular platform 96 having wheels or casters 98 (e.g., preferably four) attached thereto. A supporting structure 99 is disposed toward the middle of the platform and is generally in the form of a substantially rectangular beam having a height similar to, and a width substantially less than, the corresponding dimensions of the temperature control systems. Support mechanisms 180 are attached to the wider dimensioned supporting structure walls to suspend corresponding temperature control systems from the supporting structure. The temperature control systems are typically disposed on the cart with respective cabinet rear walls 20 in facing relation to enable brackets 124 to interface the support mechanisms attached to supporting structure 99. The support mechanisms may be attached to, and suspend temperature control systems from, the supporting structure in substantially the same manner described above for FIG. 6. The temperature control systems function in substantially the same manner described above, whereby the temperature control systems may heat various medical items and be transportable, via the cart, to various locations.

Figure 10:
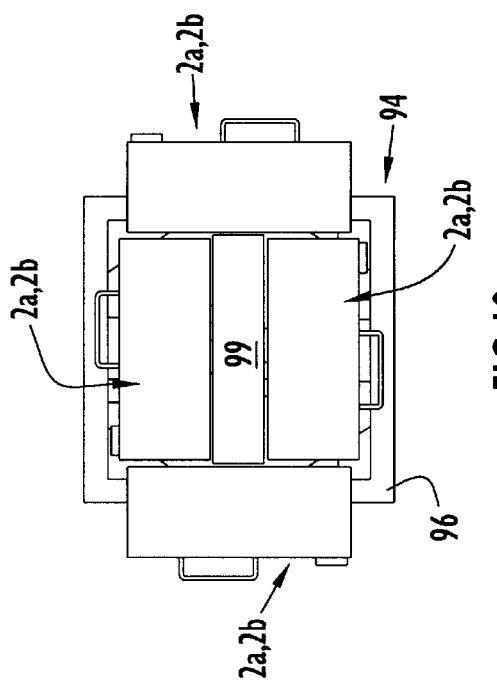
FIG. 10 is a top view of a configuration for mounting four temperature control systems on a transportable cart according to the present invention.

An alternative configuration for disposing four temperature control systems on transportable cart 94 is illustrated in FIG. 10. Specifically, supporting structure 99 is disposed toward a middle portion of platform 96 and is generally in the form of a substantially rectangular beam having height and width dimensions similar to the corresponding dimensions of the temperature control systems. Each temperature control system may be implemented by any of the temperature control systems 2a, 2b described above. A support mechanism 180 (FIG. 6) is attached to each of the vertically extending supporting structure walls. Temperature control systems 2a, 2b are positioned such that brackets 124 interface a corresponding support mechanism 180 to suspend the temperature control systems from the supporting structure. The support mechanisms may be attached to, and suspend the temperature control systems from, the supporting structure in substantially the same manner described above for FIG. 6. The temperature control systems function in substantially the same manner described above, whereby the temperature control systems may heat various medical items and be transportable, via the cart, to various locations.

Figure 11:
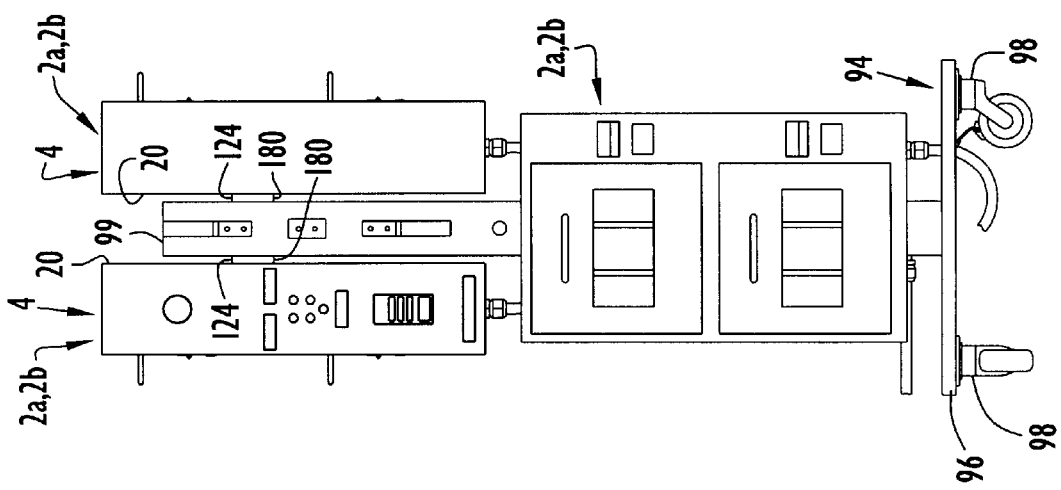
FIG. 11 is a view in perspective of an alternative configuration for mounting four temperature control systems on a transportable cart according to the present invention.

The temperature control systems described above may further be arranged in stacked relation on transportable cart 94 as illustrated in FIG. 11. Specifically, supporting structure 99 is disposed toward a middle portion of platform 96 and may include a plurality of stacked supporting structure units each in the form of a substantially rectangular beam and having height and width dimensions similar to the corresponding dimensions of the temperature control systems. Alternatively, the supporting structure may be implemented by an integral unit in the form of an elongated substantially rectangular beam having a width dimension similar to the width dimension of the temperature control systems, but a varying height dimension similar to the combined height dimensions of a plurality of temperature control systems to facilitate a stacked temperature control system arrangement. Each temperature control system may be implemented by any of the temperature control systems 2a, 2b described above. The supporting structure is configured in the form of a tower having a plurality of vertically arranged levels with each level including support mechanisms 180 attached to the vertically extending walls of the supporting structure to suspend temperature control systems 2a, 2b. The support mechanisms may be attached to, and suspend temperature control systems from, the supporting structure at each level in substantially the same manner described above for FIG. 6.

The tower configuration may be basically formed by a plurality of the above-described configurations arranged one atop the other. By way of example only, the tower configuration illustrated in FIG. 11 is generally constructed of a plurality of the configurations described above for FIGS. 8–9, and includes two levels each having two temperature control systems. However, the tower configuration may include any quantity of levels with each level having any quantity of associated temperature control systems arranged in any configuration. The temperature control systems may be implemented by any of the temperature control systems described above, and may heat various medical items and be transportable, via the cart, to various locations. Alternatively, the above-described temperature control system configurations for the transportable cart may be implemented on any suitable stationary or mobile structure.

The temperature control system configurations described above may further include an intravenous pole and/or other equipment disposed on a temperature control system, supporting structure or transportable device. Further, the pole and/or equipment may include any quantity of temperature control systems attached to the pole and/or equipment, and may be disposed on the transportable device to suspend the temperature control systems with or without the use of the supporting structure. Moreover, the supporting structure may include a plurality of supporting structure units arranged in various configurations (e.g., arranged in a triangular, circular or polygonal fashion) or be of any cross-sectional shape, and include corresponding supporting mechanisms to suspend various quantities of temperature control systems. In addition, the configurations described above may be arranged in stacked relation in any fashion (e.g., a circular supporting structure or structure arrangement may be stacked with a triangular or polygonal supporting structure or structure arrangement, etc.).

It will be appreciated that the embodiments described above and illustrated in the drawings represent only a few of the many ways of implementing a temperature control system and method for heating and maintaining medical items at desired temperatures.

The temperature control systems and components may be of any size or shape and may be constructed of any suitable materials. The controllers, fuses, power switches and labels may be disposed on the systems at any suitable locations. The systems may include any quantity of each component, while the components (e.g., cabinet, circuitry, drawers, etc.) may be arranged in any fashion. The temperature control systems may include any quantity (e.g., at least one) of drawers with each drawer having any quantity (e.g., at least one) of sub-compartments. The drawers may be of any size or shape and may be constructed of any suitable materials. The drawers may include any conventional or other handle disposed at any location, and may include any conventional or other pivoting or sliding mechanisms to facilitate placement and removal of drawers and items within the systems. The drawer sub-compartments may be of any quantity, size or shape, while the drawers and sub-compartments may each contain any quantity of any types of medical items. The drawers may include a window of any shape or size, or be implemented without a window. The window may include any type of transparent or translucent material, and may be defined at any suitable locations on the drawer, door or cabinet. Further, the drawers may be implemented by any types of drawers that are capable of being placed and removed within the system (e.g., substantially horizontal drawers, such as those in common desks), while the system may include any quantity or combination of different types of drawers. Moreover, the drawers, sub-compartments or other receptacles may be disposed within the cabinet interior chambers on shelves or other structures for receiving the medical items.

The temperature sensor may be implemented by any conventional resistive or other type of temperature sensing device, and may be disposed at any location on the drawer or cabinet interior. The heating element may include any type of configuration covering the entirety or a portion of the drawer bottom wall (e.g., strips, bars, segments, include various openings, etc.). The heating element may be implemented by any quantity of conventional or other types of heating devices (e.g., heating coils, etc.), and may be disposed on the drawer at any locations. The heating element may include any type of conventional or other connector to facilitate heating element connections, and may be fastened to the drawer via any conventional or other fastening techniques (e.g., adhesives, brackets, etc.).

The control circuitry may be implemented by any quantity of conventional or other circuit components capable of performing the above-described functions. The relay may be implemented by any conventional solid state or other type of relay device. Similarly, the cut-out switch may be implemented by any conventional or other type of switching or power limiting device. The fuses may be implemented by any conventional or other types of cut-off or switching devices, while the power switches may be implemented by any conventional or other switching devices (e.g., momentary, button, etc.) The system may include any quantity of controllers, each controlling any quantity of drawers and accommodating any quantity of set points. The controllers may each be implemented by any conventional or other processor or circuitry to control the heating elements.

The support mechanism may be of any shape or size, and may be constructed of any suitably sturdy materials. The support mechanism may include any configuration suitable to interface a member disposed at any location on a temperature control system, or suitable to interface a temperature control system directly. The support mechanism may further be connected to any structure via any conventional or other fastening techniques, and may be configured to accommodate any quantity of temperature control systems. The support mechanism base may be of any shape or size, may be constructed of any suitable materials, may include any quantity of holes of any shape or size defined at any location, and may utilize any quantity and type of fastener of any shape or size to mount the support mechanism on a structure. The engagement member may be integral with the base or be a separate unit attached to the base via any conventional or other fastening techniques. The engagement member may be of any shape or size, may be constructed of any suitable materials and may be disposed in any fashion and at any locations on the base.

The bracket may be of any shape or size, may be disposed at any suitable locations on a temperature control system via any conventional or other fastening techniques, and may be constructed of any suitably sturdy materials. The bracket may include any type of configuration suitable to interface the support mechanism or other support device. The support mechanism and bracket may be implemented by any conventional or other securing or suspension devices, and may be utilized to mount a temperature control system on any type of supporting structure.

The support frame plates may be of any shape or size, and may be constructed of any suitable materials. The plates may be connected to any pole-type or other structure of any cross-sectional shape via any conventional or other fastening techniques. The plates may include any quantity of holes of any shape or size defined at any location, and may utilize any quantity and type of fastener of any shape or size (e.g., washers, nuts, bolts, etc.) to interconnect the plates and mount the support mechanism on the support frame and pole or other structure. The plates may include a groove or channel of any shape or size to interface any type of pole or other structure. The grooves may be defined at any locations in one or more of the plates, or the plates may be configured to surround or engage the pole or other structure. The support frame may be implemented by any type of conventional or other securing devices to mount a support device on the pole or other structure.

An intravenous pole and/or other equipment may be disposed at any locations on the temperature control systems, supporting structure or transportable device. The pole and/or equipment may include any quantity of temperature control systems attached to the pole and/or equipment, and may be disposed on the transportable device to suspend the temperature control systems with or without the use of the supporting structure. The supporting structure may be of any size or shape, may be constructed of any suitable materials and may be disposed at any locations on the cart. The support structure may include a plurality of supporting structure units arranged in various configurations (e.g., arranged in a triangular, circular or polygonal fashion), be of any cross-sectional shape, and include any quantity of support mechanisms or other devices at any locations to suspend various quantities of temperature control systems.

The temperature control system configurations may include any quantity or combination of the temperature control systems described above arranged in any fashion. The temperature control system configurations described above may be arranged in stacked relation in any fashion (e.g., a circular supporting structure or structure arrangement may be stacked with a triangular or polygonal supporting structure or structure arrangement, a two system configuration may be stacked with a four system configuration, etc.).

The cart may be of any size or shape, may include any quantity of wheels or other devices disposed at any locations on the cart enabling cart motion. The cart may be implemented by any conventional or other type of transportable device. Alternatively, the temperature control systems may include rollers, casters, wheels or other rolling type structures disposed at any locations to enable the systems to be transportable. In addition, the temperature control system configurations for the transportable cart may be implemented on any suitable stationary or mobile structure.

It is to be understood that the present invention is not limited to the specific configurations or applications described above, but may be implemented by any system including independently controlled chambers or compartments that evenly distribute heat from a heat source to various types of medical or other items within the compartments via the compartment walls. Further, the support mechanism of the present invention may be utilized for mounting any system treating or handling various types of medical items on any type of supporting structure.

From the foregoing description it will be appreciated that the invention makes available a novel temperature control system and method for heating and maintaining medical items at desired temperatures wherein medical items placed within the system are uniformly heated to the same or different desired temperatures.

Having described preferred embodiments of a new and improved temperature control system and method for heating and maintaining medical items at desired temperatures, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A temperature control system for heating medical items to desired temperatures comprising:
   a system housing;
   a heating chamber disposed within said housing for receiving at least one medical item and heating said at least one medical item to a desired temperature, wherein said heating chamber includes:
   a medical item support structure to support said at least one medical item within said heating chamber and including at least one receptacle each for receiving a corresponding medical item and heating said corresponding medical item to said desired temperature, wherein said each receptacle is defined by a first thermally conductive wall and a plurality of secondary thermally conductive walls and said medical item support structure is manipulable relative to said housing to facilitate entry and removal of said at least one medical item within said system;
   a temperature sensor for measuring a temperature of said heating chamber; and
   a heater for applying heat to said first wall of each said receptacle;
   wherein said secondary walls of said each receptacle are arranged to conduct heat from the first wall of said each receptacle and distribute said conducted heat about said corresponding medical item contained within that receptacle to heat said corresponding medical item to said desired temperature; and
   a controller to facilitate entry of said desired temperature for said heating chamber and to control said heater to heat said at least one medical item to said desired temperature in response to said temperature measured by said temperature sensor.

2. A temperature control system for heating medical items to desired temperatures comprising:
   a system housing;
   a heating chamber disposed within said housing for receiving at least one medical item and heating said at least one medical item to a desired temperature, wherein said heating chamber includes:
     at least one receptacle each for receiving a corresponding medical item and heating said corresponding medical item to said desired temperature, wherein said each receptacle is defined by a first thermally conductive wall and a plurality of secondary thermally conductive walls;
     a temperature sensor for measuring a temperature of said heating chamber;
     a heater for applying heat to said first wall of each said receptacle; and
     a drawer having said at least one receptacle and a pivoting mechanism for pivoting said drawer relative to said housing to facilitate entry and removal of said drawer within said system;
     wherein said secondary walls of said each receptacle are arranged to conduct heat from the first wall of said each receptacle and distribute said conducted heat about said corresponding medical item contained within that receptacle to heat said corresponding medical item to said desired temperature; and
   a controller to facilitate entry of said desired temperature for said heating chamber and to control said heater to heat said at least one medical item to said desired temperature in response to said temperature measured by said temperature sensor.

3. The system of claim 2 wherein said drawer includes a window to enable viewing of said at least one medical item within said heating chamber during heating.

4. The system of claim 1 wherein said heater is configured to cover a portion and less than the entirety of said first wall of said each receptacle.

5. A temperature control system for heating medical items to desired temperatures comprising:
  a system housing;
  a plurality of heating chambers disposed within said housing each for receiving at least one medical item and heating said at least one medical item to a corresponding desired temperature, wherein said each heating chamber includes:
    a medical item support structure to support said at least one medical item within that heating chamber and including at least one receptacle each for receiving a corresponding medical item and heating said corresponding medical item to said corresponding desired temperature, wherein said each receptacle is defined by a first thermally conductive wall and a plurality of secondary thermally conductive walls;
    a temperature sensor for measuring a temperature of that heating chamber; and
    a heater for applying heat to said first wall of each said receptacle;
    wherein said secondary walls of said each receptacle are arranged to conduct heat from the first wall of said each receptacle and distribute said conducted heat about said corresponding medical item contained within that receptacle to heat said corresponding medical item to said corresponding desired temperature; and
  a plurality of controllers each associated with a respective heating chamber to facilitate entry of a desired temperature for that heating chamber and to control said heater of said respective heating chamber to heat at least one medical item contained within that heating chamber to said corresponding desired temperature in response to a temperature measured by said temperature sensor associated with said respective heating chamber.

6. The system of claim 5 wherein at least two of said heating chambers are associated with different respective desired temperatures.

7. The system of claim 1 further including:
  a plurality of said heating chambers each for receiving at least one medical item and heating said at least one medical item to a corresponding desired temperature;
  wherein said controller facilitates entry of a desired temperature for each heating chamber and controls said heater of said each heating chamber to heat said at least one medical item contained within that heating chamber to said corresponding desired temperature in response to a temperature measured by said temperature sensor associated with that heating chamber.

8. A temperature control system for heating medical items to desired temperatures comprising:
  a system housing;
  a plurality of heating chambers disposed within said housing each for receiving at least one medical item and heating said at least one medical item to a corresponding desired temperature, wherein at least two of said heating chambers are associated with different respective desired temperatures and said each heating chamber includes:
    a medical item support structure to support said at least one medical item within that heating chamber and including at least one receptacle each for receiving a corresponding medical item and heating said corresponding medical item to said corresponding desired temperature, wherein said each receptacle is defined by a first thermally conductive wall and a plurality of secondary thermally conductive walls;
    a temperature sensor for measuring a temperature of that heating chamber; and
    a heater for applying heat to said first wall of each said receptacle;
    wherein said secondary walls of said each receptacle are arranged to conduct heat from the first wall of said each receptacle and distribute said conducted heat about said corresponding medical item contained within that receptacle to heat said corresponding medical item to said corresponding desired temperature; and
  a controller to facilitate entry of a desired temperature for each heating chamber and to control said heater of said each heating chamber to heat said at least one medical item contained within that heating chamber to said corresponding desired temperature in response to a temperature measured by said temperature sensor associated with that heating chamber.

9. A temperature control system for heating medical items to desired temperatures comprising:
  a system housing;
  medical equipment fastened to said system housing;
  a heating chamber disposed within said housing for receiving at least one medical item and heating said at least one medical item to a desired temperature, wherein said each heating chamber includes:
    at least one receptacle each for receiving a corresponding medical item and heating said corresponding medical item to said desired temperature, wherein said each receptacle is defined by a first thermally conductive wall and a plurality of secondary thermally conductive walls;
    a temperature sensor for measuring a temperature of said heating chamber; and
    a heater for applying heat to said first wall of each said receptacle;
    wherein said secondary walls of said each receptacle are arranged to conduct heat from the first wall of said each receptacle and distribute said conducted heat about said corresponding medical item contained within that receptacle to heat said corresponding medical item to said desired temperature; and
  a controller to facilitate entry of said desired temperature for said heating chamber and to control said heater to heat said at least one medical item to said desired temperature in response to said temperature measured by said temperature sensor.

10. A temperature control system for heating medical items to desired temperatures comprising:
  a system housing;
  a heating chamber disposed within said housing for receiving at least one medical item and heating said at least one medical item to a desired temperature, wherein said heating chamber includes:
    at least one receptacle each for receiving a corresponding medical item and heating said corresponding medical item to said desired temperature, wherein said each receptacle is defined by a first thermally conductive wall and a plurality of secondary thermally conductive walls;

a temperature sensor for measuring a temperature of said heating chamber; and a heater for applying heat to said first wall of each said receptacle;

wherein said secondary walls of said each receptacle are arranged to conduct heat from the first wall of said each receptacle and distribute said conducted heat about said corresponding medical item contained within that receptacle to heat said corresponding medical item to said desired temperature;

a controller to facilitate entry of said desired temperature for said heating chamber and to control said heater to heat said at least one medical item to said desired temperature in response to said temperature measured by said temperature sensor; and a support mechanism to suspend said system from a support structure.

11. The system of claim 10 wherein said support mechanism includes:

a structure member disposed on said support structure and having a base and an engagement member protruding from said base; and a system member disposed on said system housing and having a receptacle for receiving said engagement member to suspend said system from said support structure.

12. The system of claim 11 wherein said support structure is an intravenous pole.

13. The system of claim 12 wherein said structure member further includes a pair of plates each having a groove defined therein, wherein said base is fastened to one of said plates and said plates are disposed about said pole with said pole positioned in said grooves to fasten said structure member to said pole.

14. The system of claim 10 further including a transportable device, wherein said support structure suspending said system is disposed on said transportable device to facilitate system mobility.

15. A temperature control system for heating medical items to desired temperatures comprising:

a support structure;

a plurality of temperature control units, wherein each temperature control unit includes:

a housing;

at least one heating chamber disposed within said housing for receiving at least one medical item and heating said at least one medical item to a desired temperature;

at least one temperature sensor for measuring a temperature of a corresponding heating chamber;

at least one heater for heating a corresponding heating chamber; and at least one controller to facilitate entry of a desired temperature for each heating chamber and to control each heater to heat said at least one medical item within said each heating chamber to said desired temperature associated with that chamber in response to said temperature measured by a corresponding temperature sensor; and a plurality of support mechanisms for suspending respective temperature control units from said support structure.

16. The system of claim 15 wherein:

said support structure includes a plurality of sequential sections;

at least one of said temperature control units is suspended from a respective section of said support structure, thereby forming respective tiers; and said tiers are arranged in stacked relation to suspend said plurality of temperature control units from said support structure.

17. The system of claim 15 further including a transportable device, wherein said support structure suspending said plurality of temperature control units is disposed on said transportable device to facilitate system mobility.

18. In a temperature control system including a system housing and a heating chamber disposed within said housing and having at least one receptacle for receiving a corresponding medical item, wherein each receptacle is defined by a first thermally conductive wall and a plurality of secondary thermally conductive walls and is manipulable relative to said housing to facilitate entry and removal of said corresponding medical item within said system, a method of heating medical items to a desired temperature comprising the steps of:

(a) receiving at least one medical item within said at least one receptacle in response to manipulation of said at least one receptacle relative to said housing;

(b) measuring a temperature of said heating chamber via a temperature sensor;

(c) applying heat to said first wall of each receptacle via a heater;

(d) conducting heat from said first wall of each receptacle, via respective secondary walls, to distribute said conducted heat about a corresponding medical item contained within that receptacle to heat said corresponding medical item to said desired temperature; and (e) facilitating entry of said desired temperature for said heating chamber, via a controller, and controlling said heater to heat said at least one medical item to said desired temperature in response to said temperature measured by said temperature sensor.

19. In a temperature control system including a system housing, a heating chamber disposed within said housing and having at least one receptacle for receiving a corresponding medical item and a drawer having said at least one receptacle, wherein each receptacle is defined by a first thermally conductive wall and a plurality of secondary thermally conductive walls, a method of heating medical items to a desired temperature comprising the steps of:

(a) receiving at least one medical item within said at least one receptacle, wherein step (a) further includes:

(a.1) pivoting said drawer relative to said housing to facilitate entry and removal of said drawer within said system;

(b) measuring a temperature of said heating chamber via a temperature sensor;

(c) applying heat to said first wall of each receptacle via a heater;

(d) conducting heat from said first wall of each receptacle via respective secondary walls, to distribute said conducted heat about a corresponding medical item contained within that receptacle to heat said corresponding medical item to said desired temperature; and (e) facilitating entry of said desired temperature for said heating chamber, via a controller, and controlling said heater to heat said at least one medical item to said desired temperature in response to said temperature measured by said temperature sensor.

20. The method of claim 19 wherein said drawer includes a window, and step (a) further includes:
(a.2) viewing said at least one medical item within said heating chamber through said window during heating.

21. The method of claim 18 wherein step (c) further includes:
(c.1) applying heat to a portion and less than the entirety of said first wall of each said receptacle.

22. The method of claim 18 further including a plurality of said heating chambers for receiving at least one medical item and a plurality of controllers associated with corresponding heating chambers, and wherein step (a) further includes:
(a.1) receiving said at least one medical item within each heating chamber;
step (b) further includes:
(b.1) measuring a temperature of each heating chamber via a corresponding temperature sensor;
step (c) further includes:
(c.1) applying heat within each heating chamber, via a corresponding heater, to said first wall of said each heating chamber receptacle;
step (d) further includes:
(d.1) conducting heat from said first wall of each heating chamber receptacle, via respective secondary walls, to distribute said conducted heat about a corresponding medical item contained within that receptacle to heat said corresponding medical item to said desired temperature; and
step (e) further includes:
(e.1) facilitating entry of a desired temperature for each heating chamber, via a corresponding controller, and controlling said heater of said corresponding heating chamber to heat said at least one medical item contained within that heating chamber to said corresponding desired temperature in response to a temperature measured by said temperature sensor associated with said corresponding heating chamber.

23. In a temperature control system including a system housing, a plurality of heating chambers each disposed within said housing and having at least one receptacle for receiving at least one medical item and a plurality of controllers associated with corresponding heating chambers, wherein each receptacle is defined by a first thermally conductive wall and a plurality of secondary thermally conductive walls, a method of heating medical items to a desired temperature comprising the steps of:
(a) receiving said at least one medical item within each heating chamber;
(b) measuring a temperature of each heating chamber via a corresponding temperature sensor;
(c) applying heat within each heating chamber, via a corresponding heater, to said first wall of each heating chamber receptacle;
(d) conducting heat from said first wall of each heating chamber receptacle, via respective secondary walls, to distribute said conducted heat about a corresponding medical item contained within that receptacle to heat said corresponding medical item to said desired temperature; and
(e) facilitating entry of said desired temperature for each heating chamber, via a corresponding controller, and controlling said heater of said corresponding heating chamber to heat said at least one medical item contained within that heating chamber to said corresponding desired temperature in response to a temperature measured by said temperature sensor associated with said corresponding heating, chamber wherein step (e) further includes:
(e.1) entering different desired temperatures for at least two of said heating chambers.

24. In a temperature control system including a system housing, a plurality of heating chambers each disposed within said housing and having at least one receptacle for receiving at least one medical item, wherein each receptacle is defined by a first thermally conductive wall and a plurality of secondary thermally conductive walls a method of heating medical items to a desired temperature comprising the steps of:
(a) receiving said at least one medical item within each heating chamber;
(b) measuring a temperature of each heating chamber via a corresponding temperature sensor,
(c) applying heat within each heating chamber, via a corresponding heater, to said first wall of each heating chamber receptacle;
(d) conducting heat from said first wall of each heating chamber receptacle, via respective secondary walls, to distribute said conducted heat about a corresponding medical item contained within that receptacle to heat said corresponding medical item to said desired temperature; and
(e) facilitating entry of a desired temperature for each heating chamber, via a controller, and controlling said heater of each said heating chamber to heat said at least one medical item contained within that heating chamber to said corresponding desired temperature in response to a temperature measured by said temperature sensor associated with that heating chamber.

25. The method of claim 24 wherein step (e) further includes:
(e.1) entering different desired temperatures for at least two of said heating chambers.

26. In a temperature control system including a system housing and a heating chamber disposed within said housing and having at least one receptacle for receiving a corresponding medical item, wherein each receptacle is defined by a first thermally conductive wall and a plurality of secondary thermally conductive walls, a method of heating medical items to a desired temperature comprising the steps of:
(a) receiving at least one medical item within said at least one receptacle, wherein step (a) further includes:
(a.1) fastening medical equipment to said housing;
(b) measuring a temperature of said heating chamber via a temperature sensor;
(c) applying heat to said first wall of each receptacle via a heater;
(d) conducting heat from said first wall of each receptacle, via respective secondary walls, to distribute said conducted heat about a corresponding medical item contained within that receptacle to heat said corresponding medical item to said desired temperature; and
(e) facilitating entry of said desired temperature for said heating chamber, via a controller, and controlling said heater to heat said at least one medical item to said desired temperature in response to said temperature measured by said temperature sensor.

27. In a temperature control system including a system housing, a heating chamber disposed within said housing and having at least one receptacle for receiving a corresponding medical item and a support mechanism, wherein each receptacle is defined by a first thermally conductive wall and a plurality of secondary thermally conductive walls, a method of heating medical items to a desired temperature comprising the steps of:

(a) receiving at least one medical item within said at least one receptacle, wherein step (a) further includes:
(a.1) suspending said system from a support structure via said support mechanism;
(b) measuring a temperature of said heating chamber via a temperature sensor;
(c) applying heat to said first wall of each receptacle via a heater;
(d) conducting heat from said first wall of each receptacle, via respective secondary walls, to distribute said conducted heat about a corresponding medical item contained within that receptacle to heat said corresponding medical item to said desired temperature; and
(e) facilitating entry of said desired temperature for said heating chamber, via a controller, and controlling said heater to heat said at least one medical item to said desired temperature in response to said temperature measured by said temperature sensor.

28. The method of claim 27 wherein said support mechanism includes a structure member disposed on said support structure and having a base and an engagement member protruding from said base, and a system member disposed on said system housing and having a receptacle, and step (a.1) further includes:
(a.1.1) receiving said engagement member within said receptacle to suspend said system from said support structure.

29. The method of claim 28 wherein said support structure is an intravenous pole and said structure member further includes a pair of plates each having a groove defined therein, wherein said base is fastened to one of said plates and step (a.1.1) further includes:
(a.1.1.1) disposing said plates about said pole with said pole positioned in said grooves to fasten said structure member to said pole.

30. The method of claim 27 wherein said system further includes a transportable device, and step (a.1) further includes:
(a.1.1) disposing said support structure suspending said system on said transportable device to facilitate system mobility.

31. In a temperature control system including a support structure, a plurality of temperature control units and a plurality of support mechanisms, wherein each temperature control unit includes a housing and at least one heating chamber disposed within said housing for receiving at least one medical item and heating said at least one medical item to a desired temperature, a method of heating numerous medical items to desired temperatures comprising the step of:
(a) suspending each temperature control unit from said support structure via a corresponding support mechanism to heat medical items placed within said units.

32. The method of claim 31 wherein said support structure includes a plurality of sequential sections, and step (a) further includes:
(a.1) suspending at least one of said temperature control units from each said section of said support structure, thereby forming respective tiers; and
(a.2) arranging said tiers in stacked relation to suspend said plurality of temperature control units from said support structure.

33. The method of claim 31 wherein said system further includes a transportable device, and step (a) further includes:
(a.1) disposing said support structure suspending said plurality of temperature control units on said transportable device to facilitate system mobility.

34. In a temperature control system having at least one receptacle each for receiving a corresponding medical item, wherein each said receptacle is defined by a plurality of walls and is manipulable relative to a system housing to facilitate entry and removal of said corresponding medical item within said system, a method of heating medical items to a desired temperature comprising the steps of:
(a) receiving at least one medical item within said at least one receptacle in response to manipulation of said at least one receptacle relative to said housing;
(b) applying heat to a first wall of each said receptacle and conducting said applied heat from said first wall to remaining walls of that receptacle to distribute said conducted heat about a corresponding medical item contained within that receptacle; and
(c) controlling said heat applied to said first wall of each said receptacle in accordance with a measured temperature of said at least one receptacle to heat said corresponding medical item to said desired temperature.

35. A temperature control system for heating items to desired temperatures comprising:
a system housing;
a plurality of heating chambers disposed within said housing each for receiving at least one item and heating said at least one item to a corresponding desired temperature, wherein at least two of said heating chambers are associated with different respective desired temperatures; and
a controller to facilitate entry of a desired temperature for each heating chamber and to control said each heating chamber to heat said at least one item contained within that heating chamber to said corresponding desired temperature.

36. In a temperature control system including a system housing and a plurality of heating chambers each disposed within said housing and receiving at least one item, a method of heating items to a desired temperature comprising the step of:
(a) facilitating entry of a desired temperature for each heating chamber, via a controller, and controlling said each heating chamber, via said controller, to heat said at least one item contained within that heating chamber to said corresponding desired temperature, wherein at least two of said heating chambers are associated with different respective desired temperatures.

* * * * *

US006259067C1

(12) EX PARTE REEXAMINATION CERTIFICATE (7469th)

United States Patent
Faries, Jr. et al.

(10) Number: US 6,259,067 C1
(45) Certificate Issued: Apr. 27, 2010

(54) TEMPERATURE CONTROL SYSTEM AND METHOD FOR HEATING AND MAINTAINING MEDICAL ITEMS AT DESIRED TEMPERATURES

(75) Inventors: Durward I. Faries, Jr., McLean, VA (US); Bruce R. Heymann, Vienna, VA (US); Calvin Blankenship, Centreville, VA (US)

(73) Assignee: Medical Solutions, Inc., Chantilly, VA (US)

Reexamination Request:
No. 90/009,424, Jun. 2, 2009

Reexamination Certificate for:
Patent No.: 6,259,067
Issued: Jul. 10, 2001
Appl. No.: 09/419,664
Filed: Oct. 15, 1999

Related U.S. Application Data

(60) Provisional application No. 60/126,651, filed on Mar. 29, 1999, and provisional application No. 60/104,635, filed on Oct. 16, 1998.

(51) Int. Cl.
*A61F 7/00* (2006.01)
*F27D 11/00* (2006.01)
*F27D 19/00* (2006.01)

(52) U.S. Cl. .................. 219/428; 219/394; 219/399; 604/114

(58) Field of Classification Search .................. None
See application file for complete search history.

(56) References Cited

U.S. PATENT DOCUMENTS 4,844,397 A 7/1989 Skakoon et al.
5,816,797 A 10/1998 Shoenfeld
5,862,672 A 1/1999 Faries, Jr. et al.

FOREIGN PATENT DOCUMENTS

WO WO 98/45658 10/1998

*Primary Examiner*—William C Doerrler

(57) ABSTRACT

A temperature control system includes a cabinet or system housing having a plurality of drawers for containing intravenous solution bags or other medical items. Each drawer is individually controlled, and generally includes a window and a plurality of sub-compartments with each sub-compartment accommodating an intravenous solution bag or other medical item. The drawers are each pivotable relative to the system housing to permit access to the sub-compartments, while the drawer windows enable the intravenous solution bags to be viewed during heating. A heating element is typically disposed beneath each drawer bottom wall to apply heat to walls of corresponding sub-compartments and evenly distribute heat to intravenous solution bags contained within those sub-compartments. Each drawer is associated with a controller that controls the heating element to apply heat to the corresponding drawer sub-compartments in accordance with a comparison between desired and measured temperatures associated with that drawer. Alternatively, the system may include a single common controller to control the heating element of each drawer based on the desired and measured temperatures associated with that drawer. The temperature control system may be mounted on a wall, intravenous (IV) pole, transportable cart or other suitable structure via a support mechanism. In addition, several temperature control systems may be mounted in a stacked or other arrangement on a transportable cart or other structure to provide heating capability for numerous medical items.

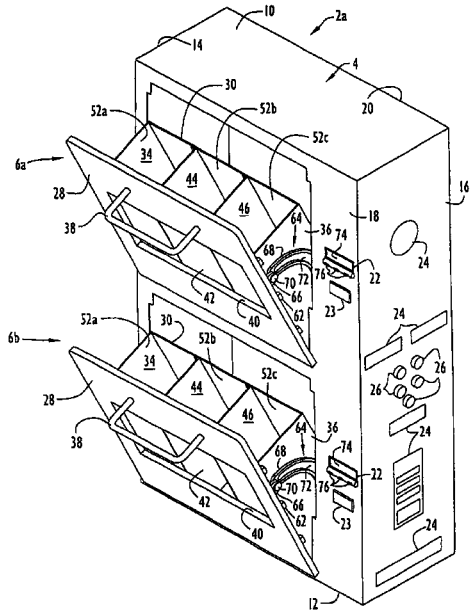

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–34 is confirmed.

Claims 35 and 36 are cancelled.

* * * * *